United States Patent
Venugopal Ambika et al.

(10) Patent No.: US 10,299,705 B2
(45) Date of Patent: May 28, 2019

(54) METHOD AND DEVICE FOR ESTIMATING SOUND RECOGNITION SCORE (SRS) OF A SUBJECT

(71) Applicant: Centre for Development of Advanced Computing (C-DAC), Thiruvananthapuram, Kerala (IN)

(72) Inventors: Vishnu Venugopal Ambika, Kerala (IN); Gopakumar Gopinathan Nair, Kerala (IN); Krishnakumar Rao Sanjeeva Rao, Kerala (IN); Biju Cheriyan Oommen, Kerala (IN)

(73) Assignee: Centre for Development of Advanced Computing, Kermala (IN)

( * ) Notice: Subject to any disclaimer, the term of this patent is extended or adjusted under 35 U.S.C. 154(b) by 349 days.

(21) Appl. No.: 15/011,965

(22) Filed: Feb. 1, 2016

(65) Prior Publication Data
US 2016/0360999 A1 Dec. 15, 2016

(30) Foreign Application Priority Data
Jun. 15, 2015 (IN) ............ 2978/CHE/2015

(51) Int. Cl.
*A61B 5/00* (2006.01)
*A61B 5/12* (2006.01)
*A61B 5/0484* (2006.01)

(52) U.S. Cl.
CPC .......... *A61B 5/123* (2013.01); *A61B 5/04845* (2013.01); *A61B 5/742* (2013.01)

(58) Field of Classification Search
CPC .................................................. A61B 5/123
See application file for complete search history.

(56) References Cited

U.S. PATENT DOCUMENTS 3,906,158 A 9/1975 Lake
2001/0049480 A1* 12/2001 John ............... A61B 5/04845
600/559

(Continued)

FOREIGN PATENT DOCUMENTS

CN 201683903 U 12/2010

OTHER PUBLICATIONS

Svard et al; The Benefit Method: Fitting Hearing Aids in Noise; Noise Health 2005; 7:12-23.

*Primary Examiner* — Sean P Dougherty
(74) *Attorney, Agent, or Firm* — Harness, Dickey & Pierce, P.L.C.

(57) ABSTRACT

Embodiments of the present disclosure disclose an estimation device for the estimation of Sound Recognition Score. The device estimates a Sound Recognition Score (SRS), to determine the hearing ability of that subject. The device also ascertains the performance of an Augmented Listening Device (ALD). The device comprises a memory unit, in which one or more audio signals and ambient noise signals are stored. The estimation device selects audio signal from the memory unit based on one or more parameters. Further, the device modulates the audio signals with the ambient noise signals and transmits the modulated audio signal to the ALD. Also, the device receives response for the transmitted signals from the ALD and estimates the responses based on the aggregate of values of the read flag data and response flag data. The estimated signal is displayed using a display unit as Sound Recognition Score.

8 Claims, 4 Drawing Sheets

(56) References Cited

U.S. PATENT DOCUMENTS

| | | | | |
|---|---|---|---|---|
| 2004/0015099 A1* | 1/2004 | Nakaichi | ............... | A61B 5/121 600/559 |
| 2004/0073136 A1* | 4/2004 | Thornton | ................ | A61B 5/12 600/559 |
| 2006/0188105 A1* | 8/2006 | Baskerville | ............ | A61F 11/08 381/60 |
| 2008/0262382 A1* | 10/2008 | Akkermans | ........... | A61B 5/117 600/559 |
| 2009/0099476 A1* | 4/2009 | Fogel | ..................... | A61B 5/121 600/559 |
| 2011/0034827 A1* | 2/2011 | Rix | ....................... | A61B 5/121 600/559 |
| 2012/0300964 A1* | 11/2012 | Ku | .................... | A61B 5/04845 381/321 |
| 2013/0303941 A1* | 11/2013 | Porges | .................. | A61B 5/125 600/559 |
| 2014/0236043 A1* | 8/2014 | Coninx | ................. | A61B 5/123 600/559 |
| 2015/0272485 A1* | 10/2015 | Navat | ................... | A61B 5/123 600/559 |
| 2015/0289062 A1* | 10/2015 | Ungstrup | ............ | H04R 25/554 381/314 |
| 2015/0359468 A1* | 12/2015 | Bochner | ............... | A61B 5/123 600/559 |
| 2016/0135719 A1* | 5/2016 | von Kraus | ............ | A61B 5/123 600/559 |
| 2016/0174880 A1* | 6/2016 | Kuk | ...................... | A61B 5/123 600/559 |

* cited by examiner

METHOD AND DEVICE FOR ESTIMATING SOUND RECOGNITION SCORE (SRS) OF A SUBJECT

FIELD

The present subject matter is related, in general to field of audiometry and more particularly, but not exclusively to a method and an estimation device to estimate sound recognition score to assess the benefit of an augmented listening device.

BACKGROUND

Many devices and methods have been arrived at for audiometric purposes for determining hearing acuity. Most of the methods and devices developed, however, have been lacking in providing for reliable and reproducible results or for accurately testing the hearing acuity of the subject being tested under the conditions which the subject normally encounters.

In the existing model, word recognition score estimations are standardized only to the intensity component of speech and often are limited to morpheme level analysis. The existing word recognition score estimation system depends on oral presentations of the stimuli by a clinician. The determination of basic hearing acuity with respect to, for example, the amplitude of a sound, such as a spoken word, which the subject can correctly identify, is not particularly difficult. However, a simple test of this nature fails to take into account important factors that determine actual hearing acuity of the subject under normal environmental conditions.

The existing tools for checking the benefit received from an augmented listening device, does not take into account the effect of background noise on the performance of the device despite it being one of the top priorities when it comes to choice of amplification.

In particular, conventional audiometer tests to determine hearing acuity does not take into account the background noises to which the subject is exposed when the acuity of the subjects hearing is most important, especially when the subject is engaged in his normal occupation. For example, a subject employed in a certain location in a factory will be exposed to certain types of background noise more or less continuously and it is under these particular conditions that the hearing acuity of the subject is important. Furthermore, each environment is accompanied by a relatively specific background noise at substantially constant sound level, and it is only in the presence of such noise that the hearing acuity of a subject can be reliably determined.

SUMMARY

The one or more shortcomings of the prior art are overcome by a method and an evaluation system as claimed and additional advantages are provided through the provision of method and the evaluation system as claimed in the present disclosure.

Additional features and advantages are realized through the techniques of the present disclosure. Other embodiments and aspects of the disclosure are described in detail herein and are considered a part of the claimed disclosure.

In an aspect of the present disclosure, a method for estimating Sound Recognition Score (SRS) of a subject is provided. The method comprises, selecting audio signals based on one or more parameters by an estimation device. Further, the method comprises, modulating the selected audio signals with ambient noise signals. Then, the method comprises, transmitting the modulated audio signals to an Augmented Listening Device (ALD). The ALD is configured with at least one ear of the subject. Also, the method comprises, receiving response for the transmitted signals from the ALD and estimating Sound Recognition Score based on the response.

In an embodiment of the present disclosure, an estimating device for estimating Sound Recognition Score (SRS) of a subject is provided. The device comprises, a processor to execute one or more instructions, a memory communicatively coupled to the processor, wherein the memory stores processor-executable instructions, which, on execution, causes the processor to perform selecting audio signals based on one or more parameters, modulating the audio signals with ambient noise signals, transmitting the modulated audio signals to an Augmented Listening Device (ALD), wherein the ALD is configured with at least one ear of the subject, receiving response for the transmitted signals from the ALD and estimating the Sound Recognition Score based on the response. The estimating device helps determine the performance of the ALD by estimating the response received for the transmitted signal.

The foregoing summary is illustrative only and is not intended to be in any way limiting. In addition to the illustrative aspects, embodiments, and features described above, further aspects, embodiments, and features will become apparent by reference to the drawings and the following detailed description.

DRAWINGS

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

Figure 1:
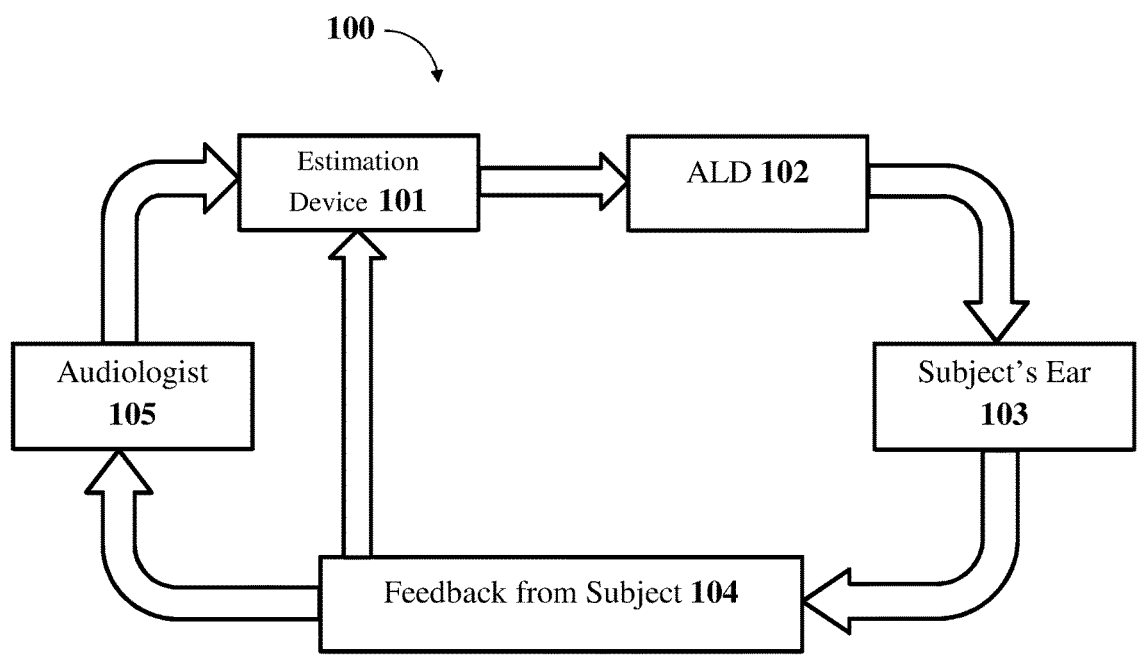
FIG. 1 illustrates an exemplary environment of test set up including an estimation device to assess the benefit of an Augmented Listening Device (ALD) in accordance with some embodiments of the present disclosure.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Embodiments of the present disclosure are related to a method and an estimation device for estimating sound recognition score of a subject to assess the benefit of an augmented listening device. The performance of the augmented listening device is measured by estimating a sound recognition score of a subject. The estimation device selects audio signals from a memory, based on one or more parameters, wherein the one or more parameters comprise language, pitch and dialect of speech. The selected audio signals are regulated based on intensity, frequency and temporal aspects of speech. The selected audio signals are modulated with ambient noise signals. The modulated audio signals are transmitted to an Augmented Listening Device (ALD). A response is received from the ALD for the transmitted signal, which is estimated to determine the performance of the ALD.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

With reference to the noise" referred to, it is understood that it may be entirely audible or it may consist of a combination of both audible and inaudible acoustic vibrations. The term noise" as used herein is thus intended to encompass any and all acoustic vibrations or emanations, whether audible or inaudible and forming a part of the environmental conditions to be simulated for test purposes.

FIG. 1 illustrates an exemplary environment of test set up 100 including an estimation device 101 to assess the benefit of an Augmented Listening Device (ALD) 102 in accordance with some embodiments of the present disclosure. FIG. 1 illustrates a test set-up 100, preferably a sound proof room. The test set up 100 comprises one or more blocks namely, an estimation device 101, an Augmented Listening Device (ALD) 102, subject's ear 103, feedback from the subject 104 and an audiologist 105. The audiologist 105 initiates a test by selecting one or more audio signals and one or more noise signals. The estimation device 101 modulates the one or more audio signals with the noise signals. Then, the estimation device 101 transmits the modulated audio signal to an Augmented Listening Device (ALD) 102, configured to at least one of the subject's ear 103. The estimation device 101 receives feedback 104 for the transmitted signal from the ALD 102, configured to the subject's ear 103 and estimates the feedback from the subject 103 as Sound Recognition Score (SRS). In an embodiment, the feedback may also be provided to the audiologist 105 for analysis.

Figure 2:
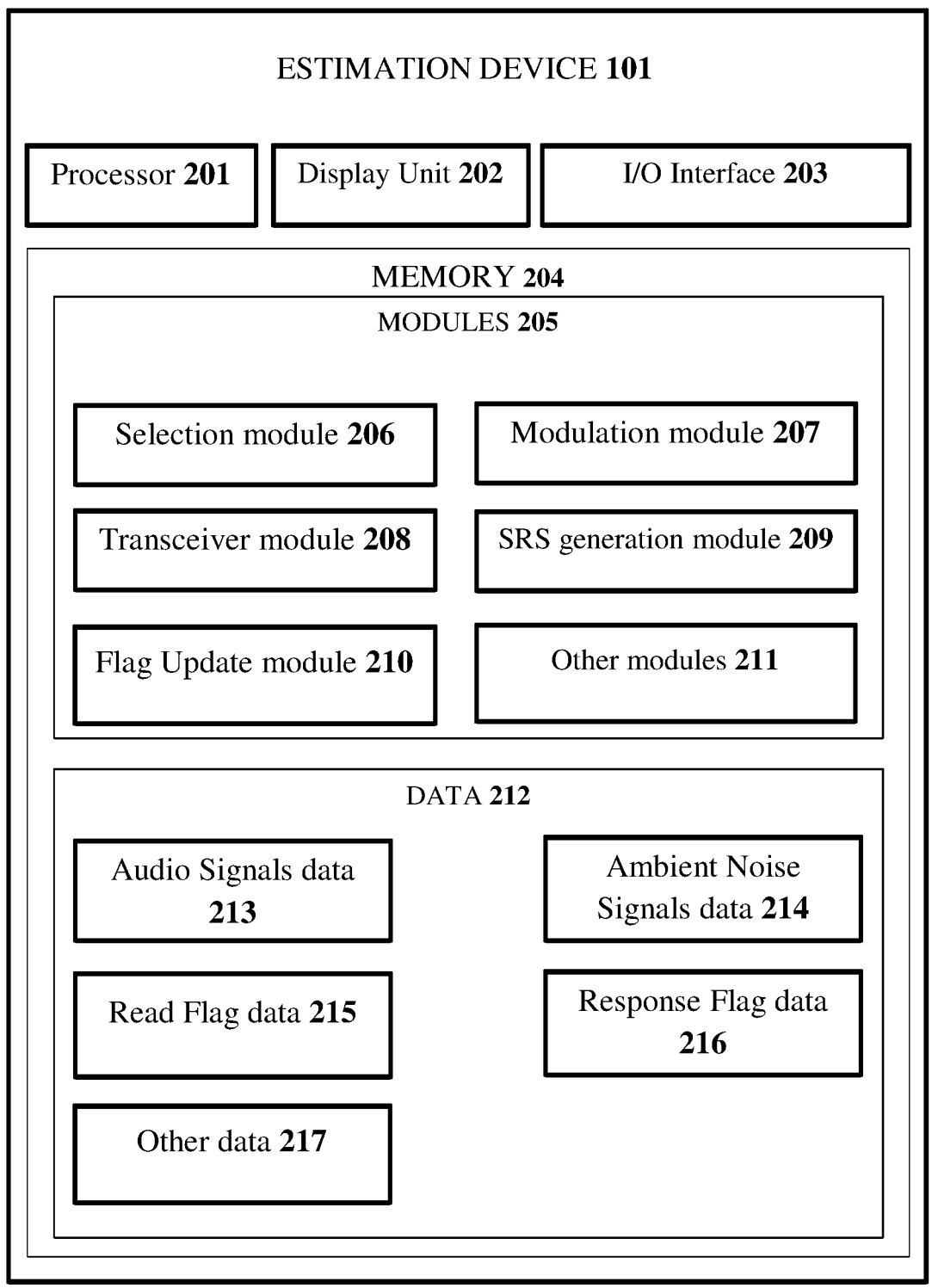
FIG. 2 shows a detailed block diagram of an estimation device to assess the benefit of an Augmented Listening Device (ALD) in accordance with some embodiments of the present disclosure.

FIG. 2 illustrates a detailed block diagram of an estimation device 101. The estimation device 101 may include at least one central processing unit ("CPU" or "processor") 201 and a memory 204 storing instructions executable by the at least one processor 201. The processor 201 may comprise at least one data processor for executing program components for executing user or system-generated requests. A user may include a person, a person using a device such as those included in this disclosure, or such a device itself. The memory 204 is communicatively coupled to the processor 201. In an embodiment, the memory 204 stores one or more data 212. The estimation device 101 further comprises an I/O interface 203. The I/O interface 203 is coupled with the processor 201 through which an input signal or/and an output signal is communicated. The estimation device 101 also comprises a display unit 202 to display the estimated SRS.

In an embodiment, one or more data 212 may be stored within the memory 204. The one or more data 212 may include, for example, audio signals data 213, ambient noise signals data 214, read flag data 215, response flag data 216 and other data 217. A specific bit of memory 204 is allocated as read flag data 215, a specific bit of memory 204 is allocated as response flag data 216, and other data 217.

In one embodiment, the audio signals data 213 may be a representation of sound, typically as an electrical voltage. The audio signals data 213 are selected from a memory 204 based on one or more parameters. The one or more parameters of the selected audio signals data 213 may include, but are not limited to, language, pitch and dialect of speech. The audio signals data 213 includes, but is not limited to a phrase, a word, syllables, and a sound across the audible spectra. In an embodiment, the audio signals 213 are standardized based on intensity, frequency and temporal aspects of speech.

In one embodiment, the ambient noise signals data 214 may be entirely audible or it may consist of a combination of both audible and inaudible acoustic vibrations. The noise referred herein may vary for different environment. The ambient noise signals data 214 are stored in a memory 204, configured in the estimation device 101.

In an embodiment, a specific bit of memory 204 is allocated as read flag data for each of the memory 204 location comprising audio signals data 213. The selected audio signal is then modulated and transmitted to the ALD 102. Upon transmission of the modulated signal, the read flag data 215 is updated from one predefined logic level to another predefined logic level.

In an embodiment, a specific bit of memory 204 is allocated as response flag for each of the memory 204 location comprising audio signals data 213. Upon reception of a response for the transmitted signal, by the estimation device 101, the response flag data 216 is updated from one predefined logic level to another predefined logic level.

In an embodiment, the data 212 in the memory 204 is processed by modules 205 of the processor 201. The modules 205 may be stored within the memory 204. In an example, the one or more modules 205, communicatively coupled to the processor 201, may also be present outside the memory 204. As used herein, the term module refers to an application specific integrated circuit (ASIC), an electronic circuit, a processor (shared, dedicated, or group) and memory 204 that execute one or more software or firmware programs, a combinational logic circuit, and/or other suitable components that provide the described functionality.

In one implementation, the modules may include, for example, a selection module 206, a modulation module 207, a transceiver module 208, a SRS generation module 209, a flag update module 210 and other modules 211. It will be appreciated that such aforementioned modules may be represented as a single module or a combination of different modules.

In an embodiment, the selection module 206 is configured in the estimation device 101 to select at least one of, audio signals data 213 and ambient noise signals data 214. The selection module 206 accesses the memory 204 based on the audio signal data 213 to be collected.

In an embodiment, the modulation module 207 modulates the audio signal data 213 with the ambient noise signal data 214. The modulation technique adapted may include, but is not limited to, analog modulation and digital modulation. Modulation comprises, varying one or more properties of a periodic waveform, called the carrier signal, with a modulating signal or the audio signal data 213 that typically contains information to be transmitted.

In an embodiment, the transceiver module 208 is configured in the estimation device 101 to transmit or receive one or more data 212. The transceiver module transmits the modulated audio signal to an ALD 102, configured to at least one ear of the subject. Also, the transceiver module 208 receives a response for the transmitted signal from the ALD 102. The transceiver module 208 may communicate with other embodiments of the present disclosure through one of, wired connection, Bluetooth, Wireless Fidelity (Wi-Fi), infrared and any other communication protocols.

In an embodiment, the SRS generation module 209 is configured to generate a sound recognition score of a subject. The SRS generation module 209 estimates the aptness of the ALD 102 by estimating the number of stimuli read and the number of responses received for each of the read stimuli. The estimated score helps in assessing performance of the ALD 102.

In an embodiment, the estimation device 101 comprises a flag update module 210, to update the read flag data 215 and the response flag data 216, when the modulated audio signal is transmitted to the ALD 102 and a response is received from the ALD 102 for the transmitted signal, respectively.

As shown in FIG. 2, the selection module 206 selects the audio signals data 213 and ambient noise signals data 214 based on the one or more parameters. The modulation module 207 modulates the audio signals data 213 with the ambient noise signals data 214. The transceiver module 208 transmits the modulated audio signal to an Augmented Listening Device (ALD) 102, wherein the ALD is configured to at least one ear of the subject. Upon transmission, the flag update module 210 updates the read flag data 215. The transceiver module 208 receives a response for the transmitted signal from the ALD 102, upon which the flag update module 210 updates the response flag data 216. The SRS generation module 209 estimates the Sound recognition Score based on the aggregate of the values of read flag data 215 and the response flag data 216. The estimated SRS is then displayed by one of, the display unit 102 or any other unit which may be configured with the estimation device 101.

The estimation device 101 may also comprise other modules 211 to perform various miscellaneous functionalities. It will be appreciated that such aforementioned modules may be represented as a single module or a combination of different modules.

Figure 3:
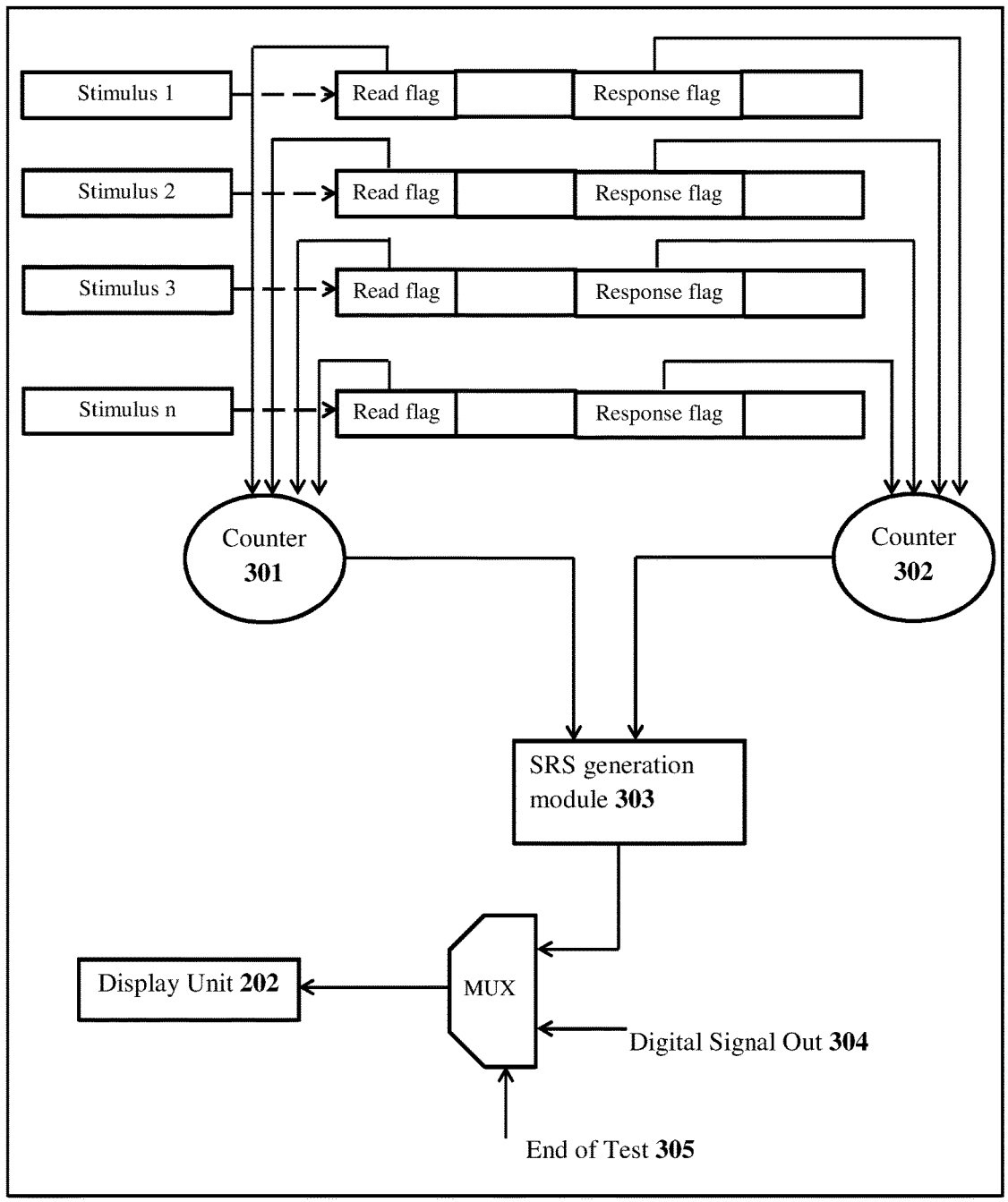
FIG. 3 shows an exemplary representation of method for estimating a Sound recognition Score (SRS) of a subject in accordance with some embodiments of the present disclosure.

FIG. 3 illustrates a method to generate SRS of a subject in accordance with some embodiments of the present disclosure. One or more audio signals data 213 and one or more noise signal data 214 are stored in the memory 204, of the estimation device 101. Each of the one or more audio signal data 213 modulated with the ambient noise signal 214 may be considered as a stimulus. A specific bit is allocated in memory 204 as read flag data 215 to monitor each of the memory location comprising the audio signals data 213. The flag update module 210 updates the read flag data 215, from one predefined logic level to another predefined logic level, upon transmission of the modulated audio signal to the ALD 102. Also, a specific bit is allocated in memory 204 as response flag data 216 to track the responses from the ALD 102. The response flag data 216 is allocated to each of the memory 204 location comprising the audio signals data 213. The flag update module 210 updates the response flag data 216 from a predefined logic level to another predefined logic level upon reception of a response for the transmitted audio signal from the ALD 102.

As shown in FIG. 3, a read flag data 215 and a response flag data 216 is associated with each of the one or more audio signals data 213 selected from the memory 204. The audio signal data 213 is modulated with the ambient noise signals data 214 and the modulated audio signals is transmitted to the ALD 102. The read flag data 215 monitors each of the stimulus transmitted. The flag update module 210 updates the status of the read flag data 215 from one predefined logic level to another predefined logic level, whenever a stimulus is transmitted to the ALD 102. The response flag data 216 monitors each of the response received from the ALD 102. The flag update module updates the response flag data 216 whenever the estimation device 101 receives a response for the transmitted signal from the ALD 102. One or more counters (301 and 302) are configured in the estimation device 101 to sum the values of the read flag data 215 and the response flag data 216, associated with each of the memory 204 location comprising the stimulus which is transmitted to the ALD 102. The values of the one or more counters (301 and 302) indicate the total number of stimuli selected by the estimation device 101 and the total response received by the estimation device 101 respectively. The SRS generation module 303 estimates the SRS of the subject based on the values of one or more counters (301 and 302). The display unit 202 displays the generated SRS only upon receiving the "end of test" signal. Also, the display unit 202 displays each of the selected stimuli from the memory 204. When a user selects one or more stimuli from the memory 204, a digital signal out signal 304 is multiplexed with each of the stimulus and is displayed by the display unit 202.

Figure 4:
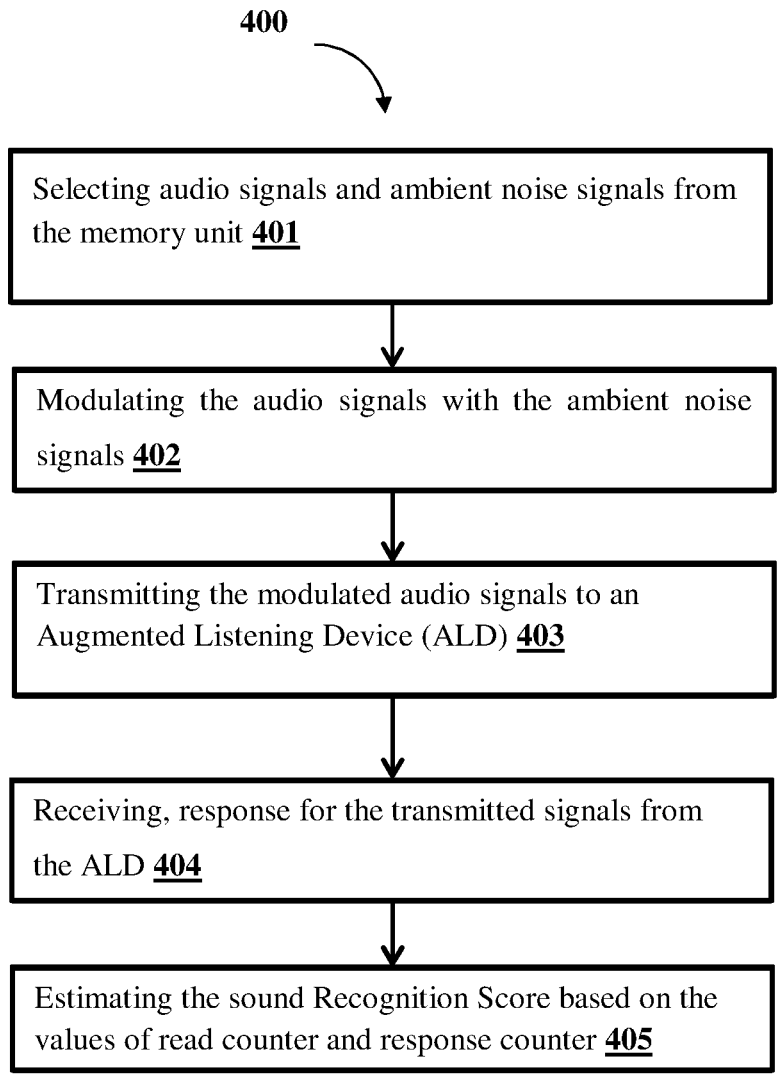
FIG. 4 shows a flowchart illustrating a method for estimating a Sound recognition Score (SRS) of a subject in accordance with some embodiments of the present disclosure.

FIG. 4 shows a flowchart illustrating a method for estimating Sound Recognition Score (SRS) 400 of a subject, in in accordance with some embodiments of the present disclosure.

As illustrated in FIG. 4, the method 400 comprises one or more blocks for estimating Sound recognition Score (SRS) 400 of a subject. The method 400 may be described in the general context of computer executable instructions. Generally, computer executable instructions can include routines, programs, objects, components, data structures, procedures, modules, and functions, which perform particular functions or implement particular abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At step 401, selecting one or more audio signals data 213 and ambient noise signals data 214 from a memory 204, based on one or more parameters. The audio signals data 213 is selected based on parameters including, but not limited to, language, pitch and dialect of speech. The selected audio signals data 213 may comprise at least one of, a phrase, a word, syllables, and a sound across the audible spectra. Further, the selected audio signals 213 are regulated based on intensity, frequency and temporal aspects of speech.

At step 402, modulate the audio signals data 213 with the ambient noise signals data 214. Modulation involves merging of two input signals, i.e. audio signals data 213 and the ambient noise signals data 214 to form a modulated signal with desirable characteristics of both the input signals.

At step 403, transmit the modulated signals to an Augmented Listening Device (ALD) 102, wherein the ALD 102 is configured with at least one ear of the subject. Transmission of the modulated signals may be through one of, wired transmission, Wireless Fidelity (Wi-Fi), Bluetooth, microwave, Infrared or any other methods compatible with the instant disclosure.

At step 404, receive response for the transmitted signal, from the ALD 102. The estimation device 101 has a feedback mechanism through which a response is received for each of the transmitted signals.

At step 405, estimating the Sound Recognition Score (SRS) by the estimation device 101, based on the values of one or more counters (301 and 302). The one or more counters (301 and 302) calculate the total number of stimuli transmitted to the ALD 102 and the total number of response received for the transmitted audio signals. The SRS generation module 209 estimates the sound recognition score of the subject based on the values of the counters (301 and 302).

In an exemplary embodiment of the present disclosure, the method comprises, selecting either a male voice or a female voice from the memory 204. A specific bit is allocated in the memory 204 as read flag data 215 to monitor each of the memory 204 location comprising the audio signals data 213. For every modulated audio signals transmitted to the ALD 102, the flag update module 210 updates the read flag data 215, from one predefined logic level to another predefined logic level, indicating that the corresponding audio signal has been read. Also, a specific bit is allocated in memory 204 as response flag data 216 for each of the memory location 204 comprising the audio signals data 213 The response flag data 216 monitors every response received for the transmitted signal, from the ALD 102. The flag update module 210 updates the response flag data 216 from a predefined logic level to another predefined logic level to indicate that a response is received for the transmitted signal, from the ALD 102. The SRS generation module 303 estimates the sound recognition score of the subject based on the values of one or more counters (301 and 302) to indicate the aptness of response. The display unit 202 displays the thus obtained percentage score as the Sound Recognition Score (SRS). Further, the estimation device 101 also has a method to resets the read flag data 215 and the response flag data 216.

Advantages of the embodiment of the present disclosure are illustrated herein.

In an embodiment, the present disclosure illustrates an estimation device to assess the performance of a person's hearing ability. The estimation device provides a better yardstick for the comparison of benefit received from an Augmented Listening Device.

In an embodiment, the present disclosure illustrates an estimation device for segregating norms for high pitch and low pitch voices.

In an embodiment, the present disclosure illustrates a test procedure, optimized with respect to intensity, frequency and temporal aspects of speech sounds.

In an embodiment, the present disclosure provides a method for generating Sound Recognition Score of a person, offering standardization with respect to dialect variation of a language.

In an embodiment, the present disclosure provides a method to demarcate the effects of background noise on the performance of the ALD.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise. The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 4 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100 | Environment of Test Set Up |
| 101 | An estimation device |
| 102 | Augmented Listening Device |
| 103 | Subject's ear |
| 104 | Feedback from subject |
| 105 | Audiologist |
| 201 | Processor |
| 203 | I/O interface |
| 205 | Modules |
| 206 | Selection module |
| 207 | Modulation module |
| 208 | Transceiver module |
| 209 | SRS generation module |
| 210 | Flag update module |
| 211 | Other module |
| 212 | Data |
| 213 | Audio signal data |
| 214 | Noise signal data |
| 215 | Read flag data |
| 216 | Response flag data |
| 217 | Other data |
| 301 | Counter |
| 302 | Counter |
| 303 | SRS generation unit |
| 304 | Digital signal out |
| 305 | End of test |
| 400 | Method to estimate SRS of a subject |

What is claimed is:

1. A method for determining performance of an Augmented Listening Device (ALD) by estimating Sound Recognition Score (SRS) of a subject, the method comprising:
   selecting, by an estimation device, a plurality of audio signals and a plurality of ambient noise signals from a memory associated with the estimation device based on one or more parameters related to speech and environment;
   generating, by the estimation device, a plurality of stimulus signals by modulating each audio signal with a corresponding ambient noise signal, wherein each stimulus signal is stored in the memory;
   transmitting, by the estimation device, each stimulus signal to the ALD, wherein the ALD is configured to provide each stimulus signal to the subject, wherein a read counter associated with the memory is updated upon transmitting each stimulus signal to the ALD;
   receiving, by the estimation device, a response for each stimulus signal transmitted to the ALD, wherein a response counter associated with the memory is updated upon each response received;
   estimating, by the estimation device, the SRS based on a cumulative sum of values of the read counter and the response counter; and
   displaying the estimated SRS on a display unit.

2. The method as claimed in claim 1, wherein the plurality of audio signals comprise at least one of a phrase, a word, syllables, and a sound across an audible spectra.

3. The method as claimed in claim 1, wherein the one or more parameters comprise language, pitch, and dialect of speech.

4. The method as claimed in claim 1, wherein the plurality of audio signals are regulated based on intensity, frequency, and temporal aspects of speech.

5. An estimating device for determining performance of an Augmented Listening Device (ALD) by estimating Sound Recognition Score (SRS) of a subject, the device comprising:
   a processor; and
   a memory communicatively coupled to the processor, wherein the memory stores processor-executable instructions, which, on execution, causes the processor to:
   select a plurality of audio signals and a plurality of ambient noise signals from the memory based on one or more parameters related to speech and environment;
   generate a plurality of stimulus signals by modulating each audio signal with a corresponding ambient noise signal, wherein the stimulus signal is stored in the memory;
   transmit each of the stimulus signals to the ALD, wherein the ALD is configured to provide each stimulus signal to the subject, wherein one or more read counters are associated with the memory and are updated upon each stimulus signal transmitted to the ALD;
   receive a response for each of the stimulus signals transmitted to the ALD, wherein one or more response counters are associated with the memory and are updated upon each response received;
   estimate the SRS based on a cumulative sum of values of the read counter and the response counter; and
   display the estimated SRS on a display unit.

6. The estimation device as claimed in claim 5, wherein the plurality of audio signals comprise at least one of a phrase, a word, syllables, and a sound across an audible spectra.

7. The estimation device as claimed in claim 5, wherein the one or more parameters comprise language, pitch, and dialect of speech.

8. The estimation device as claimed in claim 5, wherein the plurality of audio signals are regulated based on intensity, frequency, and temporal aspects of speech.

* * * * *